United States Patent [19]
Kelly

[11] Patent Number: 5,743,872
[45] Date of Patent: Apr. 28, 1998

[54] LIMITED BACKFLOW REFLUX VALVE AND METHOD

[75] Inventor: Larry Kelly, Fairfield, Ohio

[73] Assignee: Liebel-Flarsheim Company, Cincinnati, Ohio

[21] Appl. No.: 841,287

[22] Filed: Apr. 29, 1997

Related U.S. Application Data

[62] Division of Ser. No. 535,771, Sep. 28, 1995, Pat. No. 5,665,074.

[51] Int. Cl.[6] .................................................. A61M 31/00
[52] U.S. Cl. ........................... 604/49; 604/93; 604/30; 604/247; 604/249; 604/183; 137/512
[58] Field of Search ................................ 604/30, 31, 37, 604/246, 247, 249, 183, 19, 27, 28, 93, 118; 137/512, 512.3

[56] References Cited

U.S. PATENT DOCUMENTS

| | | | |
|---|---|---|---|
| 3,957,051 | 5/1976 | Topham | 128/278 |
| 4,210,173 | 7/1980 | Choksi et al. | 7/7 |
| 4,246,932 | 1/1981 | Raines | 7/7 |
| 4,341,224 | 7/1982 | Stevens | 128/675 |
| 4,546,791 | 10/1985 | Huang | 137/512 |
| 4,668,215 | 5/1987 | Allgood | 604/30 |
| 4,729,401 | 3/1988 | Raines | 7/7 |
| 5,034,000 | 7/1991 | Freitas et al. | 604/30 |
| 5,129,416 | 7/1992 | Ackroyd | 137/218 |
| 5,148,828 | 9/1992 | Farnham | 137/454.6 |
| 5,423,751 | 6/1995 | Harrison et al. | 7/7 |

Primary Examiner—Corrine M. McDermott
Assistant Examiner—Cris L. Rodriguez
Attorney, Agent, or Firm—Wood, Herron & Evans, L.L.P.

[57] ABSTRACT

A limited backflow reflux valve for connection between a syringe, catheter, and bulk container of injection fluid. The reflux valve permits injection of fluid from the syringe through the catheter into the patient, and also permits refilling of the syringe from the bulk container, without disconnection of any tubing. The reflux valve also permits a limited volume of fluid to backflow from the catheter into the syringe, so that the catheter may be checked for patency, but prevents any further backflow along this path after this limited volume. Therefore, the limited backflow reflux valve not only permits injection through the catheter, but also permits both withdrawal of blood from the patient and refilling of the syringe from the bulk contrast media container, without requiring disconnection of the catheter or other tubing and without risk of contamination of the syringe or introduction of air, increasing the efficiency of the injection process, enhancing safety, and reducing waste of injection fluid.

5 Claims, 3 Drawing Sheets

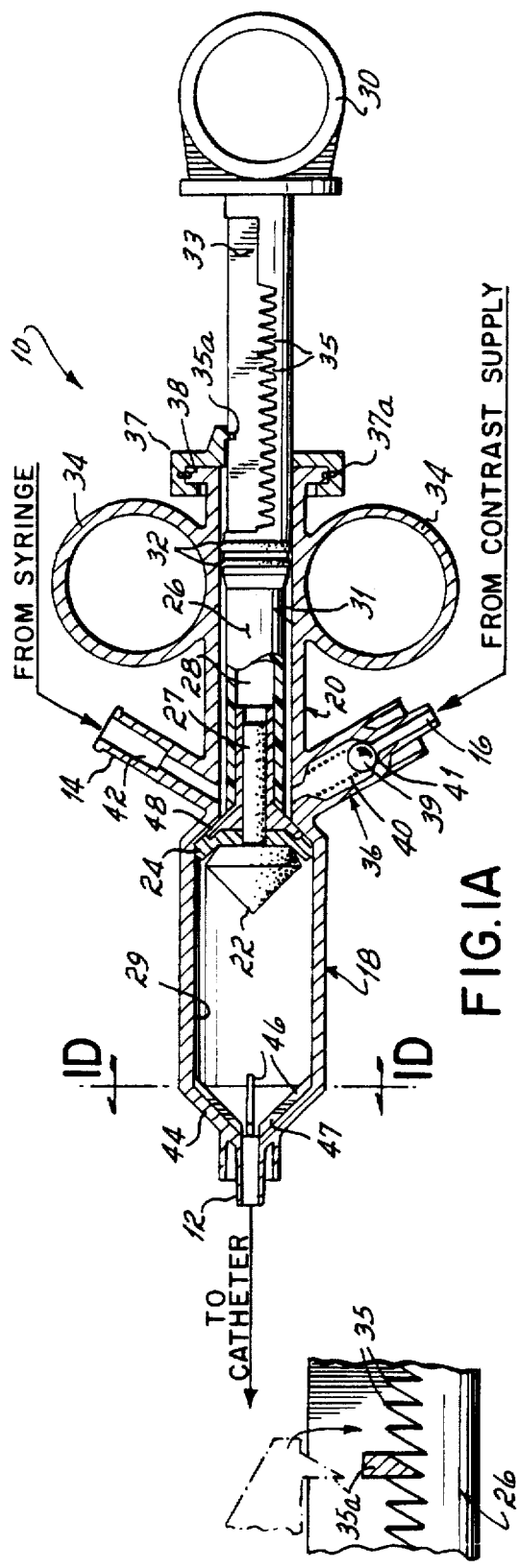
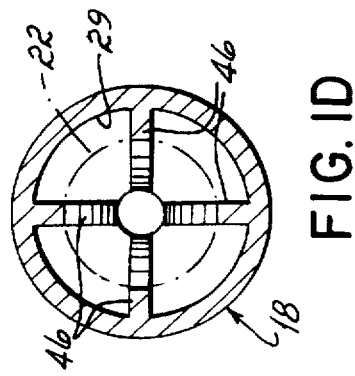
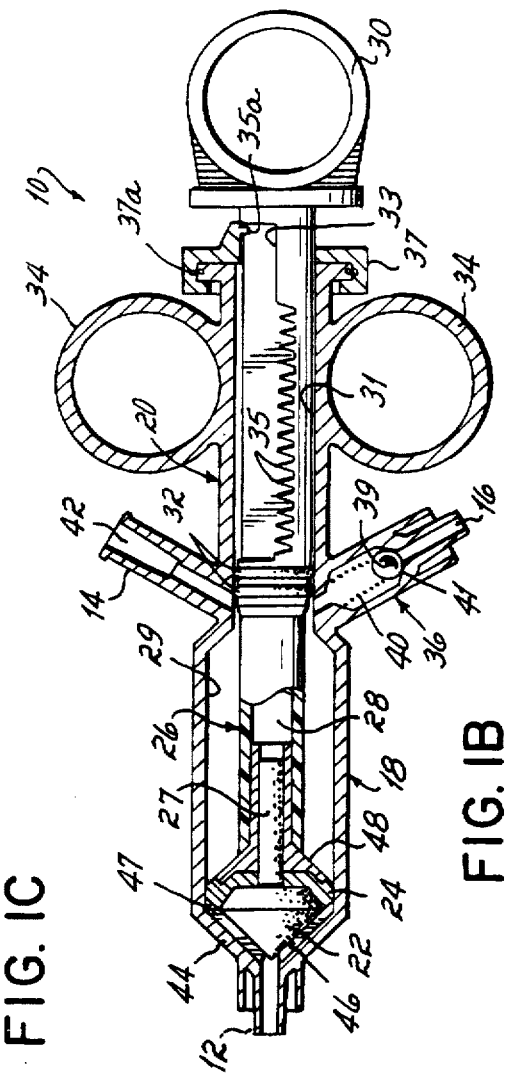

5,743,872

1

LIMITED BACKFLOW REFLUX VALVE AND METHOD

This is a division of application Ser. No. 08/535,771 filed on Sep. 28, 1995, now U.S. Pat. No. 5,665,074 entitled LIMITED BACKFLOW REFLUX VALVE.

FIELD OF THE INVENTION

The present invention relates to valve mechanisms for injection of fluid into animals through a catheter.

BACKGROUND OF THE INVENTION

In many medical environments, a medical fluid is injected into a patient during diagnosis or treatment. One example is the injection of contrast media into a patient to improve CT, Angiographic, Magnetic Resonance or Ultrasound imaging, using a powered, automatic injector. The contrast media used in these applications is typically expensive and therefore is preferably conserved to the extent possible.

During injections of this kind, it is typical for the injector operator to first mount a syringe to the injector and fill the syringe with contrast media from a separate bulk contrast media container. Then, one end of a translucent tube is coupled to the syringe, and the other end of the tube is connected to a needle or catheter and inserted into the patient, permitting subsequent injection of contrast media into the patient.

Often, during the procedure, the operator briefly withdraws blood from the patient into the catheter to check for patency of the catheter, by running the injector backward to withdraw blood from the catheter or needle and into the translucent tube. If blood is visible in the catheter after this brief withdrawal, the operator can confirm that the needle or catheter is not obstructed, for example by blood clots. Thereafter, the operator proceeds with the injection, by running the injector forward to force contrast media from the syringe into the patient.

In angiographic applications, often small injections of contrast media are made during final positioning of the catheter, in order to visualize the vasculature of the patient and position the catheter in relation to that vasculature. (Small contrast media injections are necessary because the catheter is not visible under fluoroscopy.)

One difficulty with the procedures described above is the need to decide, early in the process, the amount of contrast media to place in the syringe. For safety reasons, any contrast media remaining in the syringe after an injection cannot be reused on another patient. Therefore, due to the cost of contrast media, it is desirable to fill the syringe with only the amount of contrast media that is needed for the injection. Unfortunately, this amount is difficult to predict accurately. Overestimation of the needed amount results in wasted contrast media. Underestimation requires that the syringe be refilled; this involves disconnecting the syringe from the tube, connecting the syringe to the bulk contrast media container, withdrawing additional contrast media into the syringe, and then reconnecting the syringe to the tube. This refilling operation is not only tedious, but it also creates safety hazards due to the possible introduction of air into the catheter during disconnection and re-connection, and possible exposure of the operator and/or contamination of the bulk container by contrast media in the syringe which has potentially been exposed to the patient's blood.

Another difficulty arises during catheter positioning, when making small injections of contrast media to aid in visualizing the vasculature of the patient. To preserve sterility, the physician typically does not directly operate the power injector, but must orally communicate commands to the injector operator; this can be difficult to coordinate because the physician is simultaneously manipulating the catheter and watching the fluoroscope. Furthermore, some power injectors for injecting contrast media are designed for high flow rate injections and cannot be precisely controlled for small volume injections. As a result, when using these injectors often more contrast than necessary may be consumed during catheter positioning.

SUMMARY OF THE INVENTION

In accordance with the invention, these difficulties in using and refilling a contrast media injector and syringe are avoided by including a limited backflow reflux valve between the syringe, tubing, and bulk container of injection fluid. This valve includes one inlet port, one outlet port, and a third, bi-directional port. A first check valve permits fluid flow only from the inlet port to the bi-directional port, and a second check valve permits fluid flow from the bi-directional port to the outlet port.

The inventive reflux valve is connected between a syringe, catheter, and bulk container of fluid, by attaching the bulk contrast media container to the inlet port, the catheter to the outlet port, and the syringe to the bi-directional port. Thus, the reflux valve permits injection of fluid into the patient from the syringe and refilling of the syringe from the bulk container, without disconnection of any tubing and without risk of contamination of the bulk contrast media container.

The inventive reflux valve also permits the withdrawal step described above; specifically, the second check valve between the bi-directional and outlet ports is a limited backflow check valve which permits a limited volume of fluid to backflow into the outlet port, but prevents any further backflow into the outlet port after this limited volume. This limited volume is sufficient to permit blood to become visible in the tubing during withdrawal from the patient.

A limited backflow reflux valve in accordance with the invention, when used in contrast media injection, permits both withdrawal of blood from the patient and refilling of the syringe from the bulk contrast media container, without requiring disconnection of the catheter from the patient and without risk of contamination of the syringe or bulk container, or introduction of air. This increases the efficiency of the injection process and also enhances its safety. Furthermore, because the syringe can be refilled by simply running the injector backward to withdraw fluid, through the limited backflow reflux valve, from the bulk contrast media container, the operator is less likely to intentionally overestimate the amount of contrast media needed for an injection, thus reducing waste of contrast media.

In various specific embodiments of the invention, the limited backflow check valve is a piston fitted in a cylinder for translation through the cylinder during forward and reverse injection of fluid. One end of the cylinder carries the inlet port and bi-directional port, and the opposite end cylinder carries the outlet port.

In one specific embodiment, the circumferential boundary of the piston is cupped to permit fluid flow around the piston and out through the outlet port, but prevent fluid flow around the piston into the reflux valve through the outlet port. In a specific enhancement of this embodiment, the reflux valve includes a hand-actuatable plunger, attached to the piston of the limited backflow check valve, and extending outside of the cylinder. This hand-actuatable plunger may be used to move the piston by hand and thereby manually pump small amounts of contrast media into the patient to assist in positioning the catheter. Since the reflux valve is sterile, the plunger can be manipulated by the physician to manually inject contrast media into the patient during catheter positioning, simplifying this procedure and also enabling the physician to inject precisely controlled volumes of contrast media (equal to the displacement of the piston in the cylinder).

The hand-actuatable plunger may be locked in placed by a suitable locking mechanism, so that the motion of the piston can be limited during power injection using the reflux valve. One specifically disclosed locking mechanism includes teeth molded into the plunger which mate with a single tooth on a movable locking member. By engaging this locking member, movement of the plunger can be prevented or limited to a small range so as to prevent or limit the amount withdrawn through the outlet port.

In an alternative embodiment, the cylinder is enlarged at the end adjacent the outlet port, permitting fluid flow around the piston when the piston is at this end of the cylinder. At any other position in the cylinder, the piston seals against the walls of the cylinder, preventing fluid flow around the piston. An elastic member produces spring tension tending to draw the piston out of the enlarged region of the cylinder, thus ensuring a seal whenever pressure is equalized and fluid is not flowing around the piston.

In either of these embodiments, the housing may include ribs which extend from the end of the housing adjacent the outlet port, and engage the piston to prevent the piston from translating fully to this end of the cylindrical housing, ensuring free flow of fluid around the piston while the piston is at this end of the housing.

In yet another specific embodiment of the invention, the limited backflow reflux valve includes a gate mounted for rotation within the reflux valve housing. The gate rotates in a first direction to permit unlimited fluid flow out of the housing through the outlet port, and in an opposite direction through a limited angle to permit a limited volume of fluid flow into the housing through the outlet port. A spring member urges the gate to a predetermined angular position within the housing to seal the second check valve in the absence of fluid flow out of the outlet port.

Other aspects of the invention include a complete powered fluid injection system including a powered injector, a bulk container of fluid, and a catheter coupled through the above-described limited backflow reflux valve.

Another aspect is a contrast media delivery system in which a bulk container of contrast is coupled to a limited backflow reflux valve such as described above.

An additional aspect is the above-described methods for injecting fluid into a patient using the limited backflow reflux valve.

The above and other aspects, objects and advantages of the present invention shall be made apparent from the accompanying drawings and the description thereof.

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

FIG. 1A is a partial cross-sectional View of a limited backflow reflux valve including a plunger and plunger lock in accordance with principles of the present invention, shown with the plunger and piston at their rearwardmost positions.

FIG. 1B is a view of the limited backflow reflux valve of FIG. 1A shown with the plunger and piston at their forwardmost positions.

FIG. 1C is a partial view of an alternative embodiment of teeth 35 and 35a.

FIG. 1D is a cross-sectional view of the valve of FIG. 1A taken on lines 1D—1D.

DETAILED DESCRIPTION OF SPECIFIC EMBODIMENTS

Figure 2A:
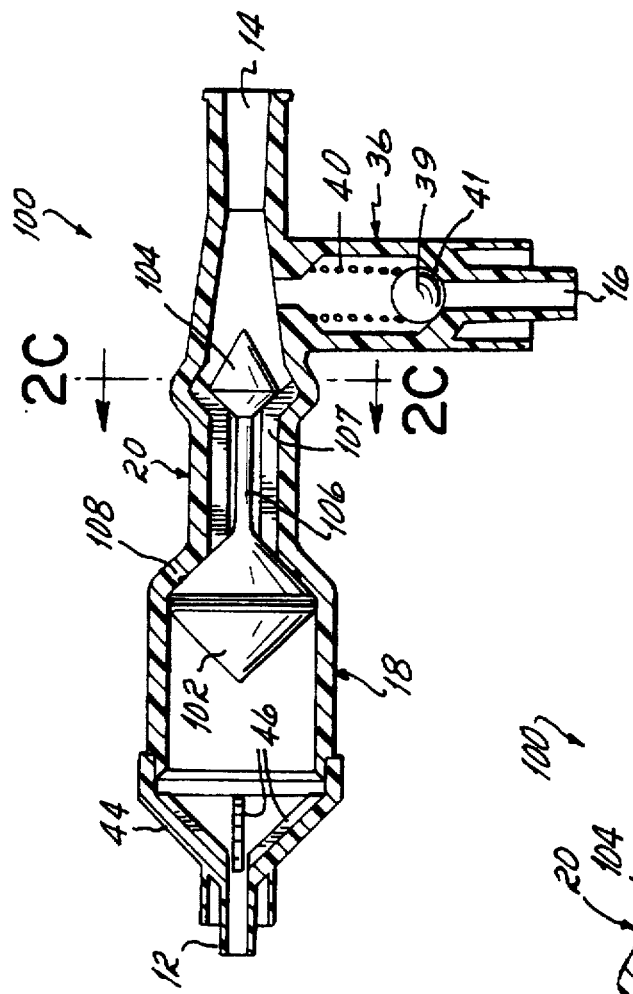
FIG. 2A is a cross-sectional view of a second embodiment of a limited backflow reflux valve in accordance with principles of the present invention, shown with the piston at its rearwardmost position.

Referring to FIGS. 1A, 1B, 1C and 1D, a limited backflow reflux valve 10 in accordance with principles of the present invention includes three ports for fluid flow into and out of the valve 10. Outlet port 12 includes a standard luer fitting sized for connection to the tubing leading to a catheter (not shown). Inlet port 16 is sized for connection to a syringe of a power injector of the type used to inject fluid into the patient. Bi-directional port 14 is sized for connection to a bulk container of contrast media via suitable tubing.

Valve 10 includes a main cylindrical housing section 18, and a second cylindrical housing section 20 having a smaller diameter than main housing section 18. A piston 22 is seated in main housing section 18 and may slide transversely through this section as shown in FIG. 1A in comparison to FIG. 1B. Piston 22 is mounted to a plunger 26 by insertion of an extension 27 at the rear of piston 22 into a recess 28 in plunger 26. Seated between piston 22 and plunger 26 is a sealing ring 24 which encircles the outer edge of piston 22 and engages the circular inner wall 29 of housing section 18 to form a fluid seal therewith.

Sealing ring 24 is manufactured of a resilient material such as rubber and is cupped at its peripheral rim; accordingly, under fluid pressure ring 24 will resiliently yield to permit fluid to flow from the rear side of ring 24 (the side from which plunger 26 extends) to the forward side of ring 24 (the side having the body of piston 22). However, if fluid pressure is removed or reversed, sealing ring 24 will re-engage the cylindrical wall 29 of section 18 and will form a fluid-tight seal preventing fluid flow in the opposite direction from the forward side of ring 24 to the rearward side of ring 24. Thus, ring 24, interacting with the cylindrical wall 29 of housing section 18, forms a check valve permitting forward fluid flow toward outlet port 12 but preventing reverse fluid flow.

Plunger 26 extends rearwardly through housing section 20, emerges from housing section 20, and terminates in a thumb grip 30. Centrally located along the length of plunger 26 is a pair of sealing rings 32 which engages the inner surface 31 of housing section 20 to form a seal therewith and prevent fluid from escaping from housing section 20. Housing section 20 has, on its outer sides, finger grips 34. Grips 30 and 34 are sized and positioned so that a physician's fingers may be placed in grips 34 and the thumb from the same hand placed in grip 30, so that plunger 26 may be manually driven into or retracted from housing sections 18 and 20.

The exterior surface of plunger 26, rearward of sealing rings 32, carries a number ofteeth 35, which extend from plunger 26 along a substantial portion of the length of plunger 26. However, a rearwardmost auto-extravasation zone 33 of plunger 26 does not bear any teeth, for reasons that will be noted below.

At the rearward end of housing section 20, a twist-lock 37 is journalled to a flange 38 on housing section 20. Twist-lock 37 carries one or more teeth 35a (one being shown in the Figs.) which can be rotated such that the tooth or teeth on twist-lock 37 mate to and engage the teeth 35 on plunger 26. Accordingly, by rotating twist-lock 37, plunger 26 may be locked in a given axial location or left free to slide axially within housing section 20. A torsion spring 37a may be included in the journalled connection between twist-lock 37 and housing section 20, producing a force tending to rotate twist-lock 37 into engagement with teeth 35 on plunger 26 and thereby lock plunger 26 in place. In one embodiment of the invention, a snap-fitting (not shown) may be included in the twist-lock 37 to permit the twist-lock 37 to be rotated and held in its unlocked position against the force of the torsion spring 37a.

In the embodiment shown in FIG. 1C, teeth 35 and 35a are barbed, such that twist-lock 37 will not prevent forward motion of plunger 26 within the housing of syringe 10, but will prevent rearward motion of plunger 26 within the housing.

The various uses and advantages of these different twist-lock embodiments will be noted below.

Inlet port 16 is in fluid communication with the interior of housing sections 18 and 20 through a check valve barrel 36. Barrel 36 communicates with tie interior of housing section 20 at a position which is always forward of sealing rings 32 even when piston 22 and plunger 26 are at their forwardmost positions (FIG. 1B). This position is also always rearward of sealing ring 24 even when piston is at its rearwardmost position (FIG. 1A).

A check valve ball 39 is positioned inside of barrel 36. A spring 40 is compressed inside barrel 36 with ball 39 to produce a positive force urging ball 39 toward the outer wall 41 of barrel 36. Barrel 36, ball 39 and spring 40 cooperate to form a check valve which permits fluid flow through inlet port 16 into the housing of valve 10 but prevents fluid flow through inlet port out of the housing of valve 10.

Bi-directional port 14 is also in fluid communication with the interior of housing section 20 via a channel 42. Channel 42 communicates with housing section 20 at a position opposite to barrel 36, i.e., at a position which is always forward of sealing rings 32 even when piston 22 and plunger 26 are at their forwardmost position (FIG. 1B) and which is always rearward of sealing ring 24 even when piston 22 is at its rearwardmost position (FIG. 1A).

Housing section 18 terminates, at its forward end, in a conical end cap 44 having a shape which is congruent to the conical piston 22. Positioned within end cap 44 are spacer ribs 46 which project inwardly from the conical surfaces of end cap 44. Four such ribs 46 are shown in FIG. 1D although fewer or more ribs could be included. When piston 22 advances to its forwardmost position as shown in FIG. 1B, the conical front surface of piston 22 rests against ribs 46, leaving a circumferential gap between the conical front surface of piston 22 and the conical interior surface of end cap 44 through which fluid may flow into outlet port 12.

Housing section 18 terminates, at its rearward end, in a second conical end cap 48 which mates with a conical surface on plunger 26. Unlike the interior surface of end cap 44, the interior surface of end cap 48 does not carry ribs or spacers, so that when the plunger is translated to its fully-rearward position, the conical surface of plunger 26 may mate fully with the conical interior surface of end cap 48 to form a fluid-tight connection.

The above-described limited backflow reflux valve 10 may be used in a number of different ways to perform an injection procedure, some of which are described below for exemplary purposes. These procedures will be described with reference to the injection of contrast media into an animal patient for the purpose of improving CT, Angiographic, Magnetic Resonance or Ultrasound imaging. Due to the cost of contrast media, the advantages of the invention are particularly dramatic in such injections; however, numerous other similar injection procedures could be performed using the above-described valve 10 with like effects.

In the injection procedure, a first step is to fill the syringe on the power injector with contrast media for the injection. This step is performed by coupling a bulk container of contrast media (such as a bag, cup, or bottle) to inlet port 16, and coupling the syringe to bi-directional port 14. Then, the power injector is run in reverse to withdraw air and fluid into the syringe. This reduces the pressure inside of housing section 18 and 20 in the region forward of sealing rings 32 and rearward of sealing ring 24. The cupped shape of sealing ring 24 causes sealing ring 24 to maintain a tight seal against housing section 18, preventing air from passing sealing ring 24.

If the frictional force of sealing ring 24 is sufficiently small, the initial pressure drop produced by reverse operation of the power injector will cause piston 22 and plunger 26 to move rearwardly through housing sections 18 and 22 toward the position shown in FIG. 1A. Piston 22 and plunger 26 will Be driven in this direction due to the lower cross-sectional area of housing section 20 as compared to housing section 18. This force will continue to act until piston 22 and plunger 26 have translated to their fully rearward position shown in FIG. 1A, at which time piston 22 and plunger 26 will cease motion.

Further pressure reduction caused by continued reverse operation of the power injector will overcome the compression force produced by spring 40, and cause ball 39 to withdraw from the outer end of check valve barrel 36, allowing air and fluid to flow from the bulk contrast media container into inlet port 16, through the housing of valve 10, and out of bi-directional port 14 into the syringe. Thereafter, continued reverse operation of the power injector will cause contrast media from the bulk container to fill the power injector syringe.

It should be noted that if the motion of piston 22 and plunger 26 are impeded, either by high friction between sealing ring 24 and housing section 18, or because twist-lock 37 has been rotated to engage with teeth 35 on plunger 26, then piston 22 and plunger 26 will not move before air and fluid are admitted into valve 10 through inlet port 16. However, sealing ring 24 is configured for low-friction operation so that plunger 26 will be drawn rearwardly prior to the introduction of fluid through inlet port 16. Furthermore, before filling the syringe through valve 10, plunger 26 should be retracted to its rearwardmost position, or alternatively twist-lock 37 should be rotated and snapped or manually held in its disengaged position, so that piston 22 and plunger 26 will translate to the position shown in FIG. 1A prior to the introduction of fluid through inlet port 16.

In one embodiment, valve 10 is supplied from the manufacturer with plunger 26 already in its fully-rearward position. In this case, it is unnecessary to move plunger 26 to its rearwardmost position or to snap or manually hold twist-lock 37 in its disengaged position during initial filling through valve 10. (Since valve 10 comes in contact with blood from the patient, it must be disposed after use; therefore, the valve 10 will only be used for one refilling procedure, and so if valve 10 is supplied with plunger 26 in its fully rearward position, the plunger 26 will be in this position during initial filling.)

As a final aside, it should be noted that if barbed teeth (FIG. 1C) are used, and valve 10 is supplied from the manufacturer with plunger 26 in its rearwardmost position, the valve 10 need not be provided with a snap for holding twist-lock 37 in its disengaged position, since in such a case all procedures requiring disengagement of twist-lock 37 are performed manually, and in such cases twist-lock 37 can be easily manually disengaged by hand in a manner described below.

When the desired amount of contrast media has been drawn through valve 10 and into the syringe, the backward motion of the power injector is terminated. At this instant, the pressure inside of valve 10 is equalized, and as a result the compression force of spring 40 forces ball 39 to engage to the outward end of check valve barrel 36, sealing inlet port 16 from the interior of valve 10.

After thus filling the power injector syringe, a length of high pressure tubing, for connection to the catheter, is attached to the outlet port 12 of valve 10. The power injector is then run forward to force any air in the syringe into valve 10 and out through the high pressure tubing. During this operation the power injector is typically tilted upwards so that any air in the power injector syringe moves to the nozzle of the syringe. Furthermore it is preferred that valve 10 be tilted upward so that outlet port 12 is elevated relative to the remainder of valve 10 so that gravity causes any air bubbles entrained in valve 10 to move to and out of outlet port 12.

As the power injector forces air and contrast media into valve 10 through port 14, a positive pressure is produced inside of housing sections 18 and 20 in the region forward of sealing rings 32 and rearward of sealing ring 24. This positive pressure tends to increase the sealing pressure on ball 39 enhancing the seal at inlet port 16. Furthermore, due to the different cross-sectional areas of housing sections 18 and 20, this positive pressure generates a forward force upon piston 22 and plunger 26 urging piston forwardly toward the position shown in FIG. 1B. The outward resilient force of the cupped outer perimeter of sealing ring 24 is sufficiently large that this positive pressure differential will cause piston 22 and plunger 26 to move forwardly to the position shown in FIG. 1B, provided twist-lock 37 does not prevent such motion.

For reasons noted below, it is desirable for the piston 22 and plunger 26 to move to the forwardmost position shown in FIG. 1B by the end of the setup procedure and before injecting fluid. Accordingly, the outward resilient force of the cupped outer perimeter of sealing ring 24 is sufficiently large that piston 22 will move forward if not impeded by twist-lock 37. If barbed teeth (see FIG. 1C) are used on twist-lock 37, then plunger 26 will freely translate in the forward direction regardless of whether twist-lock 37 is disengaged. However, if the teeth 35 and 35a are not barbed (see FIGS. 1A and 1B), then twist-lock 37 should be held open during initial bubble removal to permit plunger 26 to move to its forwardmost position.

After piston 22 and plunger 26 reach their forwardmost positions shown in FIG. 1B, further forward motion of the power injector increases pressure inside of valve 10, ultimately overcoming the resilient force produced by sealing ring 24 and permitting air and contrast media to flow around piston 22 and into conical end cap 44 and out of outlet port 12 into the tubing connected thereto.

After sufficient forward motion of the power injector, all air in the syringe, valve 10 and tubing can be expelled, so that the system is prepared for use in injection. Accordingly, the tubing at outlet port 12 may be connected to the catheter and the catheter inserted into the patient.

As noted above, in some injection procedures, it is desirable to inject a small amount of contrast media to aid in visualizing the vasculature of the patient and positioning the catheter. To permit this operation, twist-lock 37 is disengaged to permit free movement of plunger 26 and piston 22. Then, to perform a small-volume injection, the physician or technician grasps valve 10 with his/her thumb and two fingers using grips 30 and 34, and manually moves plunger 26 and piston 22 rearwardly and forwardly to pump small amounts of contrast media through the catheter and into the patient. For this operation, twist-lock 37 must be disengaged, which can be done by rotating twist-lock 37 with a third finger on the same hand used to grasp grips 30 and 34.

When piston 22 is manually urged rearwardly, a positive pressure is developed inside the housing of valve 10 in the region rearward of sealing ring 24. When this pressure reaches a sufficient level, it overcomes the resilient force produced by the cupped exterior of sealing ring 24, permitting contrast media to flow around piston 22 from the rearward side of sealing ring 24 to the front side of sealing ring 24. Thereafter, when piston 22 is manually urged forwardly, a positive pressure is developed inside of valve 10 in the region forward of sealing ring 24. This positive pressure enhances the seal of sealing ring 24, such that no fluid may flow around sealing ring 24. Accordingly, when the pressure reaches a level greater than the patient's blood pressure, contrast media is injected from the portion of valve 10 forward of sealing ring 24 into the patient through the catheter. At the same time, as piston 22 moves forward, a negative pressure is developed in the portion of valve 10 rearward of sealing ring 24. This negative pressure eventually overcomes the compression force of spring 40, such that additional contrast media is supplied to valve 10 through inlet port 16.

Through the above interactions, contrast media may be injected into the patient in small, measured quantities by repeated forward and reverse motion of plunger 26.

After the catheter has been properly positioned, a large-scale injection of contrast media may be performed by activating the power injector. Doing so will cause contrast media to flow into valve 10 through bi-directional port 14, initially translating piston 22 to its forwardmost position (if twist-lock 37 is disengaged or has barbed teeth) and thereafter forcing fluid flow around sealing ring 24. (Once sealing ring 24 has been deflected by forward flow of fluid through valve 10, the cross-sectional area of the gap between sealing ring 24 and the interior of housing section 18 is larger than the cross-sectional area of the syringe nozzle and tubing; therefore, valve 10 does not produce any substantial resistance to fluid flow at even high flow rates.)

As noted below, it may be desirable for plunger 26 to be placed in its fully-forward position during an injection procedure. If barbed teeth are used, such positioning will be automatically achieved from the natural motion of plunger 26 in response to fluid pressures in the valve 10. However, if barbed teeth are note used, plunger 26 must be manually moved to its fully-forward position, or twist-lock 37 must be disengaged during injection so that plunger 26 naturally moves forward in response to fluid pressures in the valve 10.

It may be desirable to position plunger 26 at its fully-forward position because, at any time during the injection procedure, the physician may wish to withdrawn blood through the catheter and into the tubing to check for patency of the catheter. To do so, the physician operates the power injector in reverse, producing a negative pressure inside of the syringe. If piston 22 and plunger 26 are at their forwardmost position, they will respond to this negative pressure by moving rearwardly (in the same manner as discussed above with respect to initial filling of the syringe), drawing blood out of the patient and into the catheter. When blood becomes visible in the tubing, it can be confirmed that the catheter is not blocked.

During this withdraw procedure, twist-lock 37 should be in position to engage with the teeth 35 on plunger 26. However, since there are no teeth in the auto-withdrawal zone 33 of the plunger 26, if plunger 26 is fully forward at the beginning of withdrawal twist-lock 37 will be unable to engage plunger 26, and plunger 26 will be able to move rearwardly out of the housing of valve 10 for a distance equal to the length of the auto-withdrawal zone. Thereafter, twist-lock 37 will engage teeth 35 in plunger 26 and prevent further movement. Thus, if plunger 26 is in its forwardmost position during injection, a controlled, limited volume of blood can be withdrawn from the patient before engagement of the twist-lock 37. Thereafter, twist-lock 37 will engage the teeth on plunger 26 and prevent further withdrawal so that further rearward motion of the power injector will not withdraw blood, but rather will draw fluid into valve 10 through inlet port 16 in the manner discussed above with respect to filling the syringe.

Thus, the twist-lock 37, interacting with plunger 26, causes a predetermined quantity of fluid (e.g., 2 ml) to be withdrawn from the patient by operation of the power injector, without the need for highly accurate operation of the power injector. This predetermined quantity can be selected to be less than the total volume of the tubing and catheter, such that blood is unable to reach valve 10, preventing contamination. However, even if blood is allowed to reach valve 10, because sealing ring 24 is tightly sealed to the interior of housing section 18 during withdrawal any blood withdrawn from the patient into valve 10 is contained within valve 10 in the region forward of sealing ring 24, avoiding contamination of either the power injector syringe connected to port 14 or the bulk contrast media container connected to port 16.

For reference, a typical small catheter for a non-angiographic procedure is about 3 inches long and 0.02 inches inside diameter, resulting in a volume of 0.015 ml captured in the catheter. A typical small catheter for an angiographic procedure is about 10 inches long and 0.03 inches inside diameter, resulting in a volume of 0.116 ml captured in the catheter. A typical large catheter (for angiographg) is 40 inches long and 0.05 inches inside diameter, resulting a volume of 1.287 ml captured in the catheter. Thus, for these typical sizes, an withdrawal of 2 ml of blood from the patient would be sufficient for blood to appear in the tubing leading to the catheter.

At any time during an injection, it may be discovered that there is insufficient contrast media remaining in the syringe to complete the procedure. In such a case, the technician need only operate the syringe in reverse, which (possibly after initial withdrawal of a limited volume of blood into the catheter) will cause additional contrast media to flow from the bulk container through inlet port 16 and refill the syringe. Thus, the syringe may be refilled at any time during the procedure, without disconnecting tubing and without risk of contamination of introduction of air.

Figure 2B:
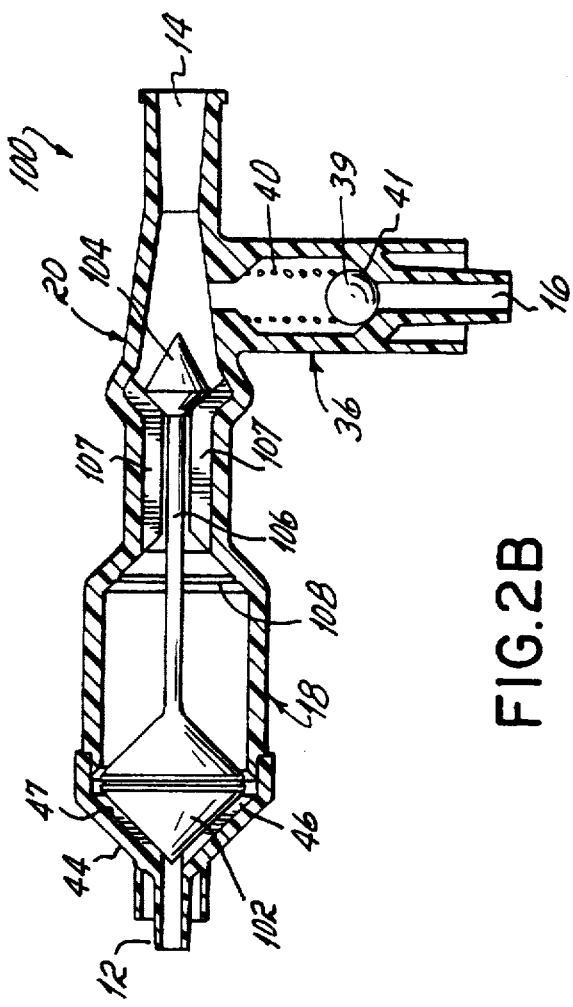
FIG. 2B is a view of the limited backflow reflux valve of FIG. 2A shown with the piston at its forwardmost position.

Referring now to FIGS. 2A and 2B, a simplified embodiment of a limited backflow reflux valve operates generally under the principles illustrated above, but without certain features. Specifically, the simplified valve 100 includes, as before, an outlet port 12 for connection to tubing leading to a catheter, a bi-directional port 14 for connection to a syringe, and an inlet port 16 for connection to a bulk container of injection fluid.

As in the embodiment of FIGS. 1A-1D, inlet port 16 includes a check valve barrel 36, ball 39 and spring 40 which collectively provide a check valve function to allow fluid to flow into valve 100 through port 16 but not outward through port 16. The housing of syringe 100 also includes a main cylindrical section 18 and a secondary section 20, and a piston 102 translates axially through section 18 in response to pressure and fluid flow within valve 100.

Unlike the embodiment of FIGS. 1A-1D, however, there is no plunger 26 extending from piston 102; rather, piston 102 freely moves within housing section 18 solely in response to fluid pressure experienced inside of valve 100. Instead of a plunger, piston 102 includes an integral rearward section which extends rearwardly through housing section 20 and terminates in a bulb 104.

Figure 2C:
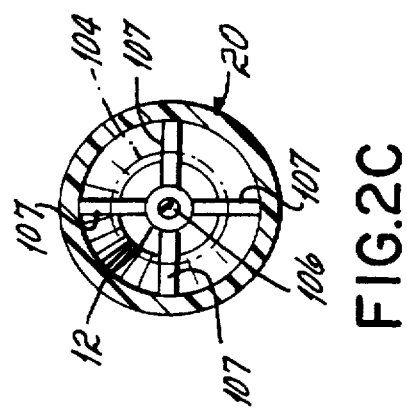
FIG. 2C is a cross-sectional view of the valve of FIG. 2A taken on lines 2C—2C.

In the embodiment illustrated in FIGS. 2A-2B, piston 102 and bulb 104, and the connecting elastic element 106, are a single, integral element, formed of a flexible material that can stretch resiliently to a great extent, such as silicon rubber. Connecting elastic element 106 provides a resilient force tending to move piston 102 rearwardly, as discussed below. To achieve this, bulb 104 is held against four ribs 107 (see FIG. 2C), positioned within housing section 20 in a manner which engages bulb 104 and prevents bulb 104 from moving forwardly toward housing section 18.

The forward end of housing section 18 includes, as before, a conical end cap 44. End cap 44 also includes ridges 46 which, as before, extend inwardly from end cap 44 and prevent piston 102 from engaging fully against end cap 44, such that a small radial gap 47 is left between piston 102 and end cap 44 even when piston 102 is at its fully forward position shown in FIG. 2B.

This forwardmost end of housing section 18 is enlarged in diameter, so that, as best seen in FIG. 2B, when piston 102 reaches its forwardmost position, the periphery of piston 102 is no longer able to seal against the internal surfaces of housing section 18, and therefore fluid is able to flow around piston 102, through the gap 47 between piston 102 and end cap 44, and out of outlet port 12. So long as fluid flow continues in this direction, piston 102 will be held against ridges 46 and will not re-engage the periphery of housing section 18. However, if the pressure equalizes and fluid flow discontinues, elastic pressure from elastic element 106 will pull piston 102 away from the forwardmost end of housing section 18, causing the periphery of piston 102 to re-seat against the cylindrical walls of housing section 18 and seal any fluid in end cap 44 and outlet port 12 from communication with housing section 18.

The rearward end of housing section 18 includes a similar conical section. This section includes a circumferential ridge 108 which engages piston 102 when piston 102 is at its rearwardmost position shown in FIG. 2A, thereby sealing piston 102 and ensuring there can be no fluid flow around piston 102 when in this rearwardmost position.

In use, the simplified limited backflow reflux valve 100 performs similarly to the valve discussed in FIGS. 1A and 1B, with the exception that there is no provision for manual injection using the valve. The procedure will again be discussed in the context of a contrast media injection, although other injection procedures could use valve 100 with like results.

As before, the first step in using the valve is to fill the syringe. For this step, a bulk container of contrast media is coupled to inlet port 16, and the syringe is coupled to bi-directional port 14. Then, the power injector is run in reverse to withdraw air and fluid into the syringe. This motion reduces the pressure inside of housing section 18 and 20 in the region rearward of piston 102. This initial pressure drop produced by reverse operation of the power injector causes piston 102 to move rearwardly through housing section 18 to the position shown in FIG. 2A, at which time piston 102 ceases motion. (As before, valve 100 is typically disposable and may be provided with piston 102 pre-positioned as shown in FIG. 2A.)

Further pressure reduction caused by continued reverse operation of the power injector will overcome the compression force produced by spring 40 and cause ball 39 to withdraw from the outer end of check valve barrel 36, causing air and fluid to flow from the bulk contrast media container into inlet port 16, through the housing of valve 100, and out of bi-directional port 14 into the syringe. Thereafter, continued reverse operation of the power injector will cause contrast media to fill the power injector syringe.

When the desired amount of contrast media has been drawn through valve 100 and into the syringe, the backward motion of the power injector is terminated. At this instant, the pressure inside of valve 100 is equalized, and as a result the compression force of spring 40 forces ball 39 to engage to the outward end of check valve barrel 36, sealing inlet port 16 from the interior of valve 100.

After thus filling the power injector syringe, a length of high pressure tubing, for connection to the catheter, is attached to the outlet port 12 of valve 100. The power injector is then run forward to force any air in the syringe into valve 100 and out through the high pressure tubing. During this operation the power injector is typically tilted upwards so that any air in the power injector syringe moves to the nozzle of the syringe. Furthermore valve 100 may be tilted upward so that outlet port 12 is elevated relative to the remainder of valve 100 so that gravity causes any air bubbles entrained in valve 100 to move to and out of outlet port 12.

As the power injector forces air and contrast media into valve 100 through port 14, a positive pressure is produced inside of the valve housing rearward of piston 102. This positive pressure generates a forward force upon piston 102 urging piston forwardly toward the position shown in FIG. 2B. Once piston 102 reaches the forwardmost position shown in FIG. 2B, air and contrast media are able to flow around piston 102 and into conical end cap 44 and out of outlet port 12 into the tubing connected thereto.

After sufficient forward motion of the power injector, all air in the syringe, valve 100 and tubing can be expelled, so that the system is prepared for use in injection. Accordingly, the tubing at outlet port 12 may be connected to the catheter and the catheter inserted into the patient.

After the catheter has been properly positioned, a large-scale injection of contrast media may be performed by activating the power injector. Doing so will cause contrast media to flow into valve 100 through bi-directional port 14, initially translating piston 102 to its forwardmost position and thereafter forcing fluid flow around piston 102 in this position.

At any time during the injection procedure, the physician may wish to withdraw blood through the catheter and into the tubing to check for patency of the catheter. To do so, the physician operates the power injector in reverse, producing a negative pressure inside of the syringe. Initially, piston 102 will be at the forward end of housing section 18, and will respond to this negative pressure by moving rearwardly (in the same manner as discussed above with respect to initial filling of the syringe), drawing blood out of the patient and into the catheter. When blood becomes visible in the tubing, it can be confirmed that the catheter is not blocked.

Once piston 102 reaches the rearwardmost position shown in FIG. 2A, further rearward motion of the power injector will draw fluid into valve 100 through inlet port 16 in the manner discussed above with respect to filling the syringe.

Thus, the valve 100 permits a predetermined quantity of fluid (e.g., 2 ml) to be withdrawn from the patient by operation of the power injector, without the need for highly accurate operation of the power injector. Furthermore, because piston 102 is tightly sealed to the interior of housing section 18 during withdrawal any blood withdrawn from the patient into valve 100 is contained within valve 100 in the region forward of piston 102, avoiding contamination of either the power injector syringe connected to port 14 or the bulk contrast media container connected to port 16.

At any time during an injection, it may be discovered that there is insufficient contrast media remaining in the syringe to complete the procedure. In such a case, the technician need only operate the syringe in reverse, which (after initial withdrawal of a limited volume of blood into the catheter) will cause additional contrast media to flow from the bulk container through inlet port 16 and refill the syringe. Thus, the syringe may be refilled at any time during the procedure, without disconnecting tubing and without risk of contamination of introduction of air.

The preceding illustrates limited backflow reflux valves in which a piston translates axially in a cylindrical housing to permit forward flow out of outlet port 12 as well as limited reverse flow into outlet port 12. However, other structures may be used to perform this function.

Figure 3A:
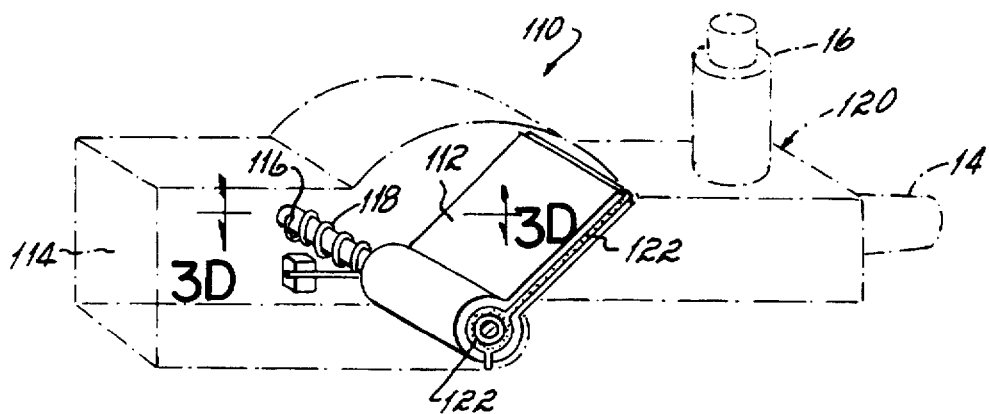
FIG. 3A is a schematic isometric view of a third embodiment of a limited backflow check valve in accordance with principles of the present invention, shown with the gate at its rearwardmost position.

For example, FIG. 3A illustrates a valve 110 including a hinged gate 112 which rotates within a fluid channel 114 to permit unlimited forward flow and limited backflow through the channel 114.

Figure 3B:
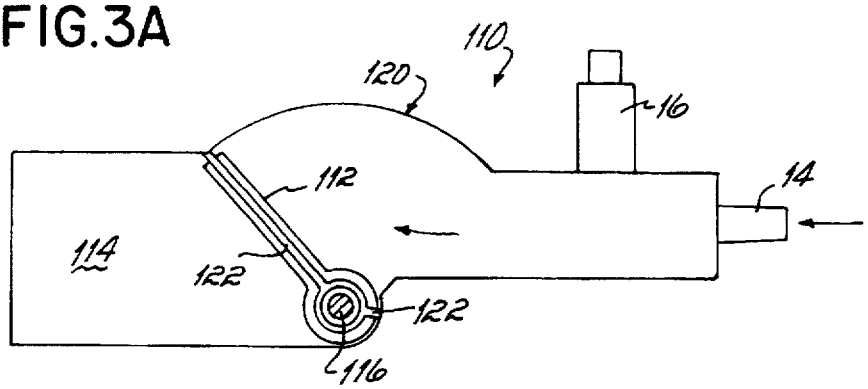
FIGS. 3B is a schematic views of the limited backflow check valve of FIG. 3A shown with the gate at the position achieved in the absence of fluid flow.
Figure 3C:
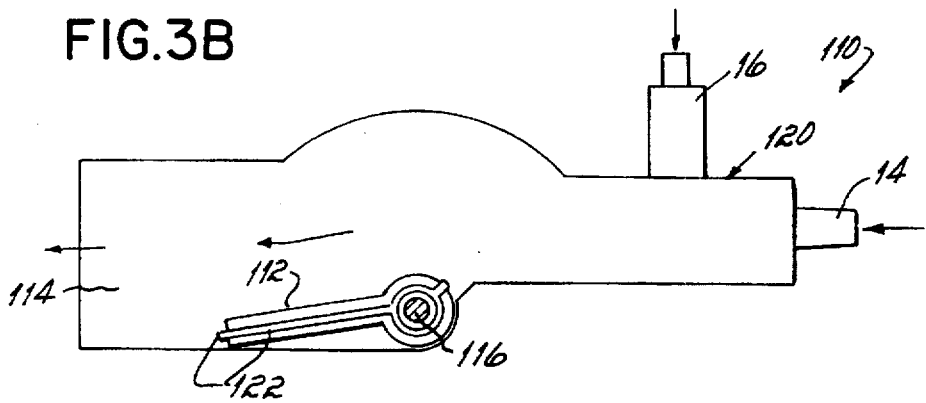
FIG. 3C is a schematic view of this valve shown with the gate at the position achieved during forward fluid flow.
Figure 3D:
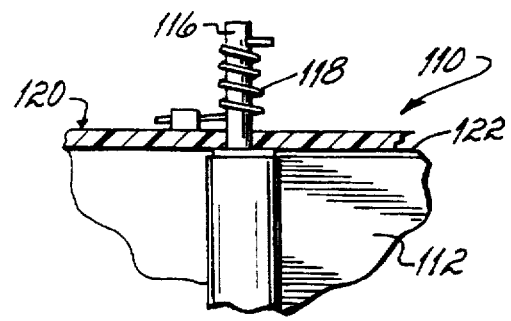
FIG. 3D is an elevation view of the axle and spring assembly of the valve of FIGS. 3A–3D.

As seen in FIGS. 3B–3D, gate 112 rotates or pivots about an axle 116 within housing 120 to perform these functions. When fluid is expelled through fluid channel 114 in the forward direction, gate 112 pivots counter-clockwise to its open position shown in FIG. 3C to permit fluid to pass unimpeded.

Whenever the pressure is equalized and fluid flow stops, however, a spring 118 mounted to the axis of rotation causes gate 112 to pivot clockwise to the sealing position shown in FIG. 3B, thus sealing the fluid channel 114.

Thereafter, if reverse fluid flow is induced in channel 114, gate 112 will pivot further counterclockwise until it reaches the position shown in FIG. 3A, at which time gate 112 engages the housing, preventing further pivoting and preventing further fluid flow. It will be noted that gate 112 carries a sealing rim 122 which seals against the interior walls of the valve housing 120 and prevents fluid flow around gate 112 when gate 112 is at or between the positions shown in FIGS. 3A and 3B.

As seen in FIG. 3D, a torsional spring 118, attached to the axle 116 of gate 112, returns gate 112 to the position shown in FIG. 3B by applying a counter-clockwise torque to gate 112.

The limited backflow check valve structure shown in FIGS. 3A-3D, or any other valve structure achieving these functions, could therefore be substituted for the piston 102 and main cylindrical housing section 18 in the embodiment of the invention shown in FIG. 2A-2B and achieve similar results.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. For example, any one of the valve structures described above could be integrally manufactured with a bulk container of contrast media, or a disposable syringe, or both, simplifying assembly and reducing cost. The various functional elements of the valve could be incorporated in a single housing, as shown in the Figs., or in separate housings interconnected by tubing. Furthermore, a cupped valve structure could be used in the simplified valve of FIGS. 2A-2B, thus permitting fluid flow around the piston in the manner discussed above with reference to FIGS. 1A-1B without necessitating the inclusion of an enlarged region in the main cylindrical housing section 18 (although such an approach might require manufacture of a two-piece piston such as is shown in FIGS. 1A-1B). Moreover, other plunger locking structures could be used in place of those illustrated in FIGS. 1A and 1B, for example a friction-engagement lock in place of a toothed lock. Also, the valve may be supplied pre-filled with contrast to simplify the procedures for initial connection and use of the valve. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A method of injecting fluid into a patient, comprising the steps of:
   providing a limited backflow reflux valve comprising
      a housing,
      an inlet port in said housing,
      an outlet port in said housing,
      a bi-directional port in said housing,
      a first check valve permitting fluid flow only into said limited backflow reflux valve housing through said inlet port, and
      a second check valve permitting fluid flow from said limited backflow reflux valve housing through said outlet port, and permitting only a predetermined limited volume of fluid to backflow through said outlet port and into said limited backflow reflux valve housing, and preventing any further backflow through said outlet port into said limited backflow reflux valve housing beyond said limited volume,
   inserting a catheter into a patient and coupling said catheter to said outlet port,
   coupling a bulk container of said fluid to said inlet port,
   coupling a syringe to said bi-directional port,
   driving a piston in said syringe forwardly to force said fluid from said syringe and into said catheter through said limited backflow reflux valve housing, and
   driving said piston in reverse in said syringe to initially extravasate said predetermined limited volume of fluid from said catheter into said limited backflow reflux valve housing, and thereafter draw fluid from said bulk container into said syringe,
   said driving steps being performed alternately without disconnection or reconnection of said syringe, catheter or bulk container from said limited backflow reflux valve.

2. The method of claim 1 wherein
   said limited backflow reflux valve is provided with a cylindrical housing,
   a piston having a circular periphery fitted in said cylindrical housing for translation through said cylindrical housing during forward and reverse flow of fluid through said outlet port to form said second check valve, and
   a plunger attached to said piston and extending externally of said cylindrical housing to permit manual translation of said piston through said cylindrical housing to manually inject fluid out of said outlet port, and
   said method further comprises the step of manually translating said piston using said plunger to manually inject quantities of fluid out of said outlet port and into said patient.

3. The method of claim 2 wherein
   said limited backflow reflux valve is provided with a lock mounted externally to said housing and movable to a first position to permit motion of said plunger within said housing and to a second position to prevent motion of said plunger within said housing,
   said method further comprises the step of moving said lock to said first position prior to manually injecting fluid into said patient, and the step of moving said lock to said second position prior to driving said piston in said syringe.

4. A contrast media supply system for use with a powered contrast media injector comprising:
   a bulk container of said contrast media,
   a limited backflow reflux valve comprising: a housing, an inlet port in said housing attached to said bulk container of fluid, an outlet port in said housing for attachment to a catheter, a bi-directional port in said housing for attachment to a syringe, a first check valve permitting fluid flow only from said bulk container into said limited backflow reflux valve housing through said inlet port, and a second check valve permitting fluid flow from said limited backflow reflux valve housing through said outlet port into said catheter, and permitting only a predetermined limited volume of fluid to backflow from said syringe through said outlet port and into said limited backflow reflux valve housing, and preventing any further backflow through said outlet port into said limited backflow reflux valve housing beyond said limited volume, whereby said powered injector may be operated forwardly to drive fluid from said syringe and into said catheter through said limited backflow reflux valve, and said power injector may be operated in reverse to initially extravasate fluid from said catheter into said limited backflow reflux valve housing and thereafter draw fluid from said bulk container into said syringe, such that fluid may be injected into said patient and said syringe may be subsequently refilled without disconnection or reconnection of said syringe, catheter or bulk container.

5. A fluid injection system for injecting fluid comprising:

a power injector having mounted thereon a syringe for holding and pressurizing said fluid, a catheter for insertion into said patient for delivery of said fluid to said patient, a bulk container of said fluid, a limited backflow reflux valve comprising: a housing, an inlet port in said housing attached to said bulk container of fluid, an outlet port in said housing attached to said catheter, a bi-directional port in said housing coupled to said syringe, a first check valve permitting fluid flow only from said bulk container into said limited backflow reflux valve housing through said inlet port, and a second check valve permitting fluid flow from said limited backflow reflux valve housing through said outlet port into said catheter, and permitting only a predetermined limited volume of fluid to backflow from said syringe through said outlet port and into said limited backflow valve housing, and preventing any further backflow through said outlet port into said limited backflow reflux valve housing beyond said limited volume, whereby said power injector may be operated forwardly to drive fluid from said syringe and into said catheter through said limited backflow reflux valve, and said power injector may be operated in reverse to initially extravasate fluid from said catheter into said limited backflow reflux valve and thereafter draw fluid from said bulk container into said syringe, such that fluid may be injected into said patient and said syringe may be subsequently refilled without disconnection or reconnection of said syringe, catheter or bulk container.

* * * * *

UNITED STATES PATENT AND TRADEMARK OFFICE
CERTIFICATE OF CORRECTION

PATENT NO. : 5,743,872
DATED : April 28, 1998
INVENTOR(S) : Larry Kelly

It is certified that error appears in the above-identified patent and that said Letters Patent is hereby corrected as shown below:

Column 3, line 12, delete "placed" and insert --place--.

Column 4, line 26, delete "views" and insert --view--.

Column 5, line 18, delete "auto-extravasation" and insert --auto-withdrawal--.

Column 5, line 47, delete "tie" and insert --the--.

Column 5, line 51, after the word "piston", insert --22--.

Column 7, line 61, after the the second "piston", insert --22--.

Column 9, line 15, delete "are note", insert --are not--.

Column 9, line 22, delete "withdrawn", insert --withdraw--.

Column 9, line 33, delete "withdraw", insert --withdrawal--.

Column 10, line 6, delete "angiograph", insert --angiography--.

Column 12, line 2, after the word "piston", insert --102--.

Signed and Sealed this

Twentieth Day of July, 1999

Attest:

Q. TODD DICKINSON

*Attesting Officer*          *Acting Commissioner of Patents and Trademarks*